United States Patent [19]

Treiber et al.

[11] Patent Number: 5,359,096
[45] Date of Patent: Oct. 25, 1994

[54] CHOLESTEROL LOWERING COMPOUNDS

[75] Inventors: Laszlo R. Treiber, Gillette; Byron H. Arison, Watchung; Shieh-Shung T. Chen, Morganville; George A. Doss, Westfield; Leeyuan Huang, Watchung; John G. MacConnell, Westfield, all of N.J.

[73] Assignee: Merck & Co., Inc., Rahway, N.J.

[21] Appl. No.: 979,559

[22] Filed: Nov. 20, 1992

Related U.S. Application Data

[63] Continuation-in-part of Ser. No. 957,350, Oct. 6, 1992, abandoned, which is a continuation-in-part of Ser. No. 715,518, Jun. 14, 1991, abandoned.

[51] Int. Cl.$^5$ ............................................. C07D 319/08
[52] U.S. Cl. ................................................... 549/363
[58] Field of Search ......................................... 549/363

[56] References Cited

U.S. PATENT DOCUMENTS

| | | |
|---|---|---|
| 5,053,425 | 10/1991 | Bartizal . |
| 5,055,487 | 10/1991 | Bartizal . |
| 5,096,923 | 3/1992 | Bergstrom et al. ................. 514/452 |
| 5,102,907 | 4/1992 | Bergstrom et al. ................. 514/456 |
| 5,132,320 | 7/1992 | Bergstrom et al. ................. 514/452 |

FOREIGN PATENT DOCUMENTS

0494622A1 7/1992 European Pat. Off. .
WO92/22660 6/1992 PCT Int'l Appl. .

*Primary Examiner*—Nicky Chan
*Attorney, Agent, or Firm*—Melvin Winokur; Catherine A. Dolan

[57] ABSTRACT

New cholesterol lowering compounds are formed from the photochemical treatment of the zaragozic acids.

26 Claims, No Drawings

CHOLESTEROL LOWERING COMPOUNDS

This is a continuation-in-part of Ser. No. 07/957,350 filed Oct. 6, 1992, now abandoned which is a continuation-in-part of PCT application US92/05/08, filed Jun. 12, 1992 which is a continuation-in-part of Ser. No. 07/715,518, filed Jun. 14, 1991 abandoned.

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e., several grams at a time and they are not very palatable.

MEVACOR (lovastatin), now commercially available, is one of a group of very active antihypercholesterolemic agents that function by limiting cholesterol biosynthesis by inhibiting the enzyme, HMG-CoA reductase.

Squalene synthetase is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol and isopentenyl t-RNA.

Previous efforts at inhibiting squalene synthetase have employed pyrophosphate or pyrophosphate analogs containing compounds such as those described in P. Ortiz de Montellano et al, *J. Med Chem.* 20, 243 (1977) and E. J. Corey and R. Volante, *J. Am. Chem. Soc.*, 98, 1291 (1976). S. Billet (U.S. Pat. No. 4,871,721) describes isoprenoid (phosphinylmethyl) phosphonates as inhibitors of squalene synthetase.

Recently certain nonphosphorus containing inhibitors of squalene synthetase have been isolated as natural products. These natrual product inhibitors are described in copending patent applications Ser. No. 496,734 filed Mar. 21, 1990, now issued as U.S. Pat. No. 5,132,320 Ser. No. 496,742 filed Mar. 21, 1990, now issued as U.S. Pat. No. 5,096,923, and Ser. No. 582,452 filed September 13, 1990, now issued as U.S. Pat. No. 5,102,907. Semisynthetic analogs of these naturally occurring compounds have been reported in copending application Ser. No. 698,766 filed May 10, 1991, A need still remains for a more effective squalene synthetase inhibitor, i.e., one that provides a greater antihypercholesterolemic effect and exhibits a good safety profile.

The natural product inhibitors are tricarboxylic acids. The present applicants have now found that these natural products known as zaragozic acid A, zaragozic acid B and zaragozic acid C undergo a photochemical reaction yielding monocarboxylic derivatives, of the zaragozic acids, which are potent cholesterol lowering agents.

DETAILED DESCRIPTION OF THE INVENTION

This invention relates to compounds of structural formula (I), (II) and (III) and compositions comprising such compounds:

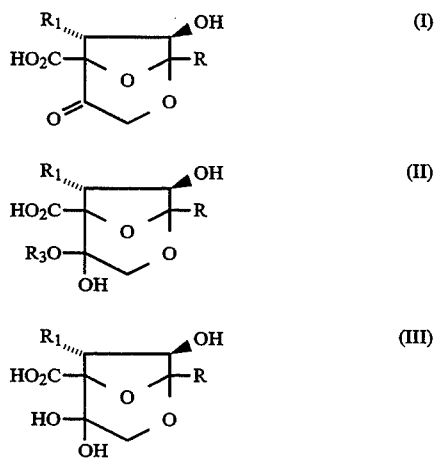

wherein
R is selected from

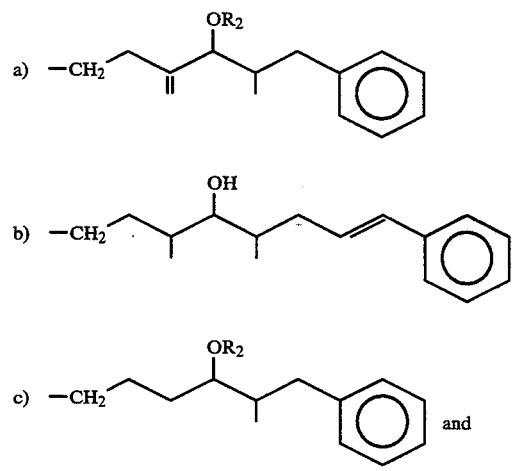

$R_1$ is selected from

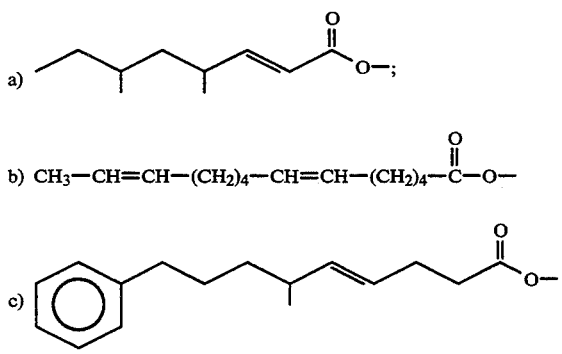

$R_2$ is selected from a) H and

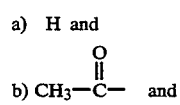

$R_3$ is $C_{1-5}$alkyl;
Provided that when R is then R₁ is

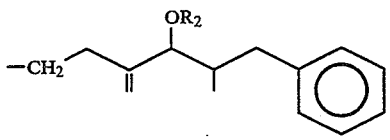

and when R is

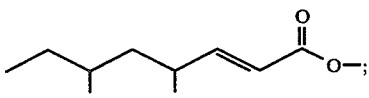

then R₁ is

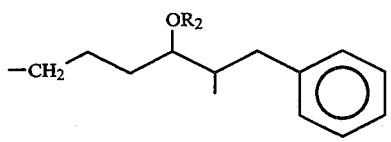

When

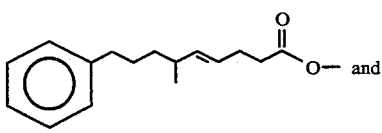

then R₁ is

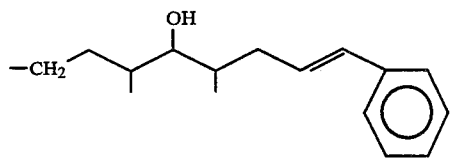

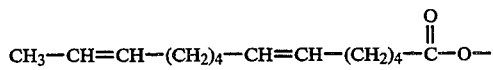

a pharmaceutically acceptable salt thereof.

Compounds and compositions of the present invention are active as squalene synthase inhibitors and are useful as cholesterol lowering agents and anti-fungal agents.

Compounds of formula (I) can be formed from zaragozic acid A (U.S. Pat. No. 5,096,923), zaragozic acid B (U.S. Pat. No. 5,132,320), and zaragozic acid C (U.S. Pat. No. 5,102,907) by photochemical treatment of the parent natural products, under exposure to air, and preferably in the presence of an appropriate catalyst such as $Fe^{3+}$, in a polar aprotic solvent such as DMSO $CH_3CN$ or DMF. Compounds of formula (I) wherein $R_2$ is acetate can be converted to compounds wherein $R_2$ is H by a biotransformation. A culture of MF6817 (ATCC 55189) has been employed in this transformation.

Compounds of formula (I) undergo a facile equilibrium to yield compounds of formula (II), in a $C_{1-5}$ alcohol such as methanol. In the presence of water they equilibrate to give compounds of formula (III). This equilibrium is established rapidly when the appropriate solvent is added to the material (I). However, the equilibrium may be shifted to predominantly (I) in acetone solution. The equilibrium may be shifted to predominantly (III) by the addition of water to the alcohol solution. Derivative (II) is most predominant in the pure alcohol solution. Thus each compound I, II, or III may be obtained substantially free of the others. Substantially free should be understood to mean in a ratio of 80:20 or higher and more particularly with respect to (I) or (II) it may mean 90:10 or higher. Thus, the compound (I) substantially free of (II) and (III) should be taken to mean that there is 10% or less of (II) and (III) present.

EXAMPLE 1

Preparation of a composition of (I), (II) and (III) wherein

R is

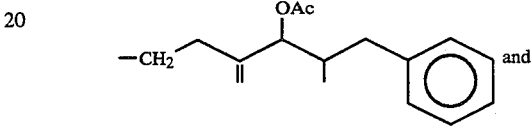

$R_1$ is

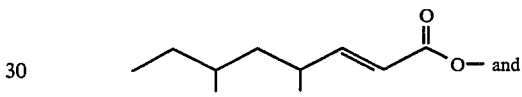

$R_3$ is methyl (Composition A)

Step A Preparation of Zaragozic Acid A

1. Culturing MF5453

Culture MF5453 (ATCC 20986) was inoculated into KF seed medium using one glass scoop of the original soil tube. The KF seed flask was incubated for 73 hours at 25° C., 220 rpm, 85% humidity. At the end of this incubation, 2.0 ml aliquots were aseptically transferred to each of 75 MBM production medium flasks. These production flasks were then incubated at 25° C., 220 rpm, 85% humidity, with a fermentation cycle of 14 days. Flasks were harvested as follows: mycelial growth was homogenized for 20 seconds at high speed using Biohomogenizer/mixer (Biospec Products Inc. Bartlesville, Okla.); and then 45 ml methanol was added to each flask (final methanol concentration was approximately 50%). Flasks were then returned to the shaker and agitated at 220 rpm for 30 minutes. Subsequently, the contents of the flasks were pooled.

2. Isolation of Compound Zaragozic Acid A

A 6 Liter 50% methanol homogenized fungal extract exhibiting a pH of 4.5 was employed in the following isolation procedure. The mycelia were filtered through celite and the recovered mycelia were extracted again by stirring overnight with 3 L of 50% methanol and again filtered.

The combined extract (9 L) of 50% methanol was diluted to 25% methanol with water (total volume 18 L) and applied to a Mitsubishi HP-20 column (750 mL) at a flow rate of 80 mL/minute. The column was washed with water (1 L) and eluted with a stepwise gradient of methanol consisting of 50/50 methanol/$H_2O$ (1 L), 60/40, methanol/$H_2O$ (1 L), 80/20 methanol/$H_2O$ (2 L), 90/10 methanol/$H_2O$ (1 L), 100% methanol (2 L), and 100% acetone (1 L). The fractions from 50/50 to 90/10 methanol/H$_2$O were combined and diluted with water to 35/65 methanol/H$_2$O (total volume 10 L).

The 10 L of 35/65 methanol/H$_2$O was acidified with 1.0N HCl (20 mL) to pH 3.0 and extracted into EtOAc (4 L). The EtOAc layer was separated and the solvent removed in vacuo to yield 260 mg of an orange oil.

A portion (10%) of the orange oil was dissolved in 1 mL methanol and diluted with 0.8 mL 10 mM potassium phosphate (pH 6.5) with some precipitation. The suspension was applied to a preparative HPLC column (Whatman Magnum 20 C$_{18}$, 22 mm ID×25 cm, 8 mL/minute. The initial mobile phase was 60/40 methanol/10 mM K$_3$PO$_4$, pH 6.5, and after 20 minutes the mobile phase was changed to 80/20 methanol/10 mM potassium phosphate, pH 6.5. Fractions of 8 mL each were collected, and the fractions from 31 to 33 minutes were combined, diluted with water to 35% methanol, acidified with 10% HCl to pH 3, and extracted into EtOAc. The solvent was removed in vacuo and a clear slightly yellow oil identified as Zaragozic Acid A was obtained.

| KF SEED MEDIUM | per liter | Trace Elements Mix | g/L |
| --- | --- | --- | --- |
| Corn Steep Liquor | 5 g | FeSO$_4$.7H$_2$O | 1.0 |
| Tomato Paste | 40 g | MnSO$_4$.4H$_2$O | 1.0 |
| Oat Flour | 10 g | CuCl$_2$.2H$_2$O | 0.025 |
| Glucose | 10 g | CaCl$_2$.2H$_2$O | 0.1 |
| Trace Element Mix | 10 mL | H$_3$BO$_3$ | 0.056 |
| pH adjusted to 6.8 (presterile) | | (NH$_4$)$_6$Mo$_7$O$_{24}$ 4H$_2$O | 0.019 |
| 50 mLs/nonbaffled 250 mLs Erlenmeyer flask | | ZnSO$_4$ 7H$_2$O | 0.2 |
| autoclave 20 minutes (121 C., 15 psi) | | dissolved in 1 L 0.6 N HCl | |

| | Medium #2 | | |
| --- | --- | --- | --- |
| MBM Products Medium | g/L | Ingredients | g/L |
| Malt extract (Difco) | 5.0 | | |
| Glucose | 15.0 | Dextrose | 4.0 |
| Peptone | 1.0 | Malt Extract (Difco) | 10.0 |
| KH$_2$PO$_4$ | 1.0 | Yeast Extract | 4.0 |
| MgSO$_4$ | 0.5 | Nutrient Broth | 4.0 |
| distilled H$_2$O | 1000.0 mls | | |
| pH 7.0 | | | |
| (no pH adjustment) | | | |
| 45 mls/nonbaffled 250 mLs Erlenmeyer flask | | | |
| autoclave 15 minutes (121 C., 15 psi) | | | |

Step B Preparation of Composition A

A solution of 2.5 mg/ml of Zaragozic acid A in dimethyl sulfoxide (DMSO) was prepared and 30 ml aliquots of this solution were placed in each of five 250 ml Erlenmeyer flasks. The samples were placed in a 37° C. incubator at a distance of 25–30 cm from a fluorescent light and were exposed to air. The reaction was allowed to continue for 6–8 days prior to isolation.

Step C Isolation Of Composition A

The five samples from Step B were combined and mixed with water (200 ml). The solution was acidified with citric acid and extracted twice with 100 ml portions of CH$_2$Cl$_2$. The combined methylene chloride phases were evaporated to an oily residue that was transferred to test tubes and evaporated further to dryness in a stream of nitrogen at 40°–50° C. The dry residues were redissolved in small volumes of methanol and combined. The methanol solution (10–15 ml) was mixed with formic acid (0.5 ml) immediately before being loaded onto a HP-20 column (2.5×23 cm, 113 ml) equilibrated with 0.5% formic acid in water. The chromatogram was developed in a stepwise gradient mode using 200 mL of each solvent mixture of water-acetonitrile beginning with volume ratios of 100:0, 90:10, etc in 10% increments up to 0:100. Each mixture contained 1 ml of formic acid. The flow rate was 3 mL/minute. The bulk of product was found in the range of 1500–1615 mL of eluate. The samples were evaporated to dryness and then redissolved in methanol to 20 mg/ml concentration used in preparative HPLC. The final purification was by preparative HPLC carried out on a Beckman Ultrasphere ODS (10×250 mm) column using 0% formic acid in acetonitrile-water (60:40 v/v) as eluant at a flow rate of 4.00 ml/min and a detector setting of 213 nm. The retention time of Composition A was found to be 15.8 minutes; for comparison the retention time of zaragozic acid A was 10.4 minutes.

$^1$H NMR (400 MHz) (Acetone) IA 4.67 (d, 17.1, 1H), 4.42 (d, 17.1, 1H) 3-CH$_2$ IIA 4.16 (d, J=12.1, 1H), 3.71 (d, 12.1, 1H) 3-CH$_2$ IIIA 4.11 (d, 13.4, 1H), 3.91 (d, 13.4, 1H) 3-CH$_2$

EXAMPLE 2

Preparation of Compound (I) wherein R is

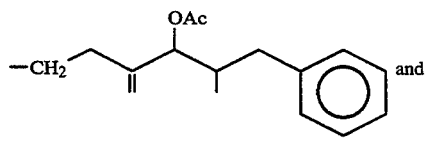

R$_1$ is

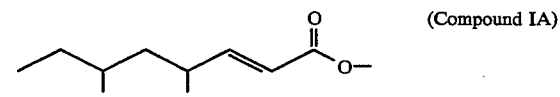

(Compound IA)

This compound was prepared by evaporating to dryness a sample of composition A from Example 1 and then dissolving the dried material in anhydrous acetone. A solution of (IA) was obtained substantially free of its equilibrium derivatives $_1$H NMR (Acetone) 4.67 (d,17.1, 1H),4.42 (d,17.1, 1H) 3-CH$_2$ $^{13}$C NMR (Acetone) 197.2, 163.5,106.8, 91.9, 82.9 80.8, 70.3

EXAMPLE 3

Preparation of a Compound (II) wherein R is

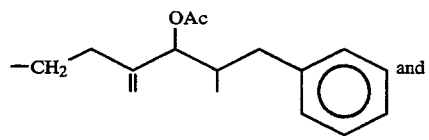

R$_1$ is

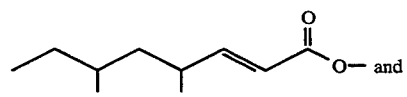

R$_3$ is methyl (Compound IIA)

This compound was prepared by evaporating to dryness a sample of composition A from Example 1 and then dissolving the dried material in pure methanol. A solution of (IIA) was obtained substantially free of its equilibrium derivatives. $^1$NMR (400 MHz) (CD$_3$OD) 4.06 (d, 13.1, 1H), 3.86 (d, 13.1, 1H) 3-CH$_2$ $^{13}$C NMR 170.8, 106.4, 93.8, 89.4, 82.8, 81.8, 63.4,

EXAMPLE 4

Preparation of a compound (III) wherein R is

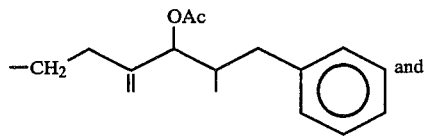

R$_1$ is

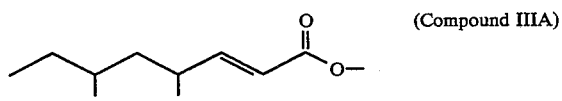

(Compound IIIA)

This compound was prepared by adding to the acetone solution of Example 3 an amount of water to bring the water concentration to about 10%. A solution of IIIA was obtained substantially free of its equilibrium derivatives.

$^{13}$C NMR (Acetone+D$_2$O) 169.7,106.1, 90.3, 88.7, 82.5, 81.4, 70.0 $^1$H NMR (400 MHz, Acetone+D$_2$O ) 4.11 (d, 13.4, 1H) 3.91 (d, 13.4, 1H) 3-CH$_2$.

EXAMPLE 5

Preparation of a compound (I) wherein R is

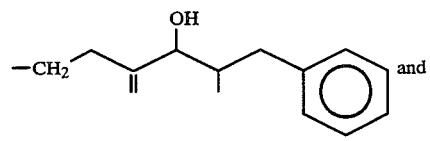

R$_1$ is

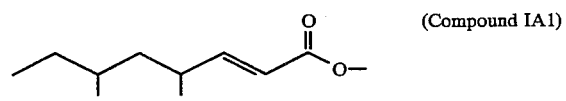

(Compound IA1)

1. Seed Growth

Medium #2 (50 ml) in 250 ml baffled flasks were inoculated with MA6817 and shaken in a rotary shaker at 220 rpm and 27° C. The seed was grown for 48 hours.

2. Fermentation

Production flasks (medium #2, 50 ml in 250 ml baffled flasks) were inoculated with 2 ml of the seed medium and shaken at 27° C. and 220 rpm on a rotary shaker. After 24 hours, a substrate containing a crude mixture of Zaragozic Acid A and Composition A, prepared above (Example 1), was added to each flask. Thus, a DMSO solution of the substrate containing Zaragozic Acid A (1.217 mg, 76.1%) and Composition A (0.382 mg, 23.9%) was used for each of two shake-flasks. Incubation continued for 72 hours.

3. Extraction

The harvested biotransformation samples were acidified with formic acid (2 ml 88% for each flask) then extracted with ethyl acetate. The organic phase was dried over Na$_2$SO$_4$ then filtered and evaporated to dryness. The dry residue was redissolved in the smallest possible volume of DMSO-water (2:1 v/v) for preparative HPLC.

4. Chromatography

Two different gradient methods were used in succession. The first separation was accomplished on a Beckman Ultrasphere Cyano column (10×25 mm) in a gradient from 20% solvent B/80% solvent A to 65% solvent B/35% solvent A in 35 minutes then at 100% solvent B for an additional 10 minutes, at a flow rate of 3.00 ml/min. Fractions were collected every 3 minutes or according to peaks detected at 213 nm, as appropriate. The selected fractions (22.5–24.0 min) were evaporated to dryness and chromatographed again on a Beckman Ultrasphere Octyl column (10×250 mm) in a gradient from 30% B/70% A to 80% B/20% A in 35 minutes then at 100% solvent B for an additional 10 minutes, at a flow rate of 3.00 ml/min. The remaining conditions were the same as in the first separation. Solvent A was 20 mM HCOOH and B was acetonitrile-water (17:3 v/v) containing the same amount of HCOOH as solvent A.

Evaporation of the selected fractions (retention time 33.6 min.) provided the product, Compound (IAI), with the following physical characteristics:

$^1$H NMR spectrum (400 mHz) (CD$_3$OD, 22° C.): 7.23 (t, 2H), 7.19 (d, 2H), 7.12 (t, 1H), 6.87 (dd, 15.7, 8.4, 1H), 5.86 (dd, 15.7, 1.0, 1H), 5.50 (d, 2.4, 1H), 5.06 (s, 1H), 4.93 (s, 1H), 4.01 (d, 2.4, 1H), 3.98 (d, 12.7, 1H), 3.89 (d, 5.0, 1H), 3.83 (d, 12.7, 1H), 2.75 (dd, 13.4, 5.9, 1H), 2.36 (dd, 13.4, 9.0, 1H), 2.0–2.45 (m, 4H), 1.93 (m, 2H), 1.1–1.4 (m, 5H), 1.03 (d, 3H), 0.86 (t, 3H), 0.85 (d, 3H), 0.79 (d, 3H) ppm.

Analytical HPLC on a Beckman Ultrasphere Octyl column (4.6×250 mm) wherein the elution was performed in the gradient mode according to the following program:

| Solvent A: | 10 mM H$_3$PO$_4$ in water | |
|---|---|---|
| Solvent B: | Acetonitrile-water (85:15 v/v) | |
| | Time (min.) | percent B |
| | 0 | 30 |
| | 2 | 30 |
| | 18 | 80 |
| | 20 | 100 |
| | 24 | 100 |
| | 25 | 30 |
| Flow: | 0.900 ml/min | |
| Temp.: | Ambient | |

Retention time of compound IAI=19.9 minutes UV max at 213 nm.

Compounds of formula (I), (II), and (III) are also useful for preparing prodrugs or other derivatives which are useful as squalene synthase inhibitors and which undergo a slower hemiketal-ketone equilibrium or do not exhibit this equilibrium at all. Specifically for compounds (I) and (III) the ketone funtionality may be converted to a cyclic ketal or mercaptal derivative using ethanediol or ethanedithiol; compounds of formula (III) may be converted to derivatives wherein the hydroxyls at C4 are etherified using two equivalents of an alkyl orthoformate ester. These derivatives and prodrugs are separately isolable and useful as cholesterol lowering agents.

The present invention is also concerned with a method of treating hypercholesterolemia which comprises the administration to a subject in need of such treatment a nontoxic therapeutically effective amount of a Compound I, II, or III, or a mixture thereof or a pharmaceutically acceptable salt thereof. Specifically, the compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients, but a daily dosage for adults is within a range of from about 20 mg to 2000 mg (preferably 20 to 100 mg) which may be given in two to four divided doses. Higher doses may be favorably employed as required.

The present invention is also concerned with a method of inhibiting squalene synthetase which comprises the administration to a subject in need of such treatment a nontoxic therapeutically effective amount of a Compound I, II, or III or a mixture thereof or a pharmaceutically acceptable salt thereof. Specifically, the compounds of this invention are useful in treating disease conditions such as, but not limited to, hypercholesterolemia conditions which require the action of the enzyme squalene snythetase. They may be administered by the same routes in the same dosages as described for the method of treating hypercholesterolemia.

The pharmaceutically acceptable salts of the compounds of this invention include those formed from cations such as sodium, potassium, aluminum, calcium, lithium, magnesium, zinc, and from bases such as ammonia, ethylenediamine, N-methylglutamine, lysine, arginine, ornithine, choline, N,N'-dibenzylethylenediamine, chloroprocaine, diethanolamine, procaine, N-benzylphenethylamine, diethylaimine, piperazine, tris(hydroxymethyl)aminomethane, and tetramethylammonium hydroxide.

The compounds of this invention may also be administered in combination with other cholesterol lowering agents such as those which inhibit an enzymatic pathway in the biosynthesis of cholesterol. Example of such agents would include but are not limited to HMG-CoA reductase inhibitors, HMG-CoA synthase inhibitors, and squalene epoxidase inhibitors. Illustrative of such inhibitors are lovastatin, simvastatin, pravastatin and fluvastatin. Other cholesterol lowering agents that may be administered include niacin, probucol, and the fibric acids, clofibrate and gemgibrozil. Appropriate daily dosages for adults are niacin (2–8 gm), probucol (up to 1000 mg), clofibrate (up to 2 gm) and gemfibrozil (800–1500 mg).

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methy-(3-trimethylaminopropyl) iminotrimethylene dihalide]. The relative amounts of the compounds of this invention and these polymers is between 1:100 and 1:15,000.

The intrinsic squalene synthetase inhibitory activity of the compounds of this invention was measured by the standard in vitro protocol described below:

PREPARATION OF HUMAN HepG2 cell ENZYME

1. SOURCE: HEPG2 CELL LINE (Liver, hepatoblastoma, Human) ATCC No. HB 8065
2. CELL GROWTH AND MAINTENANCE Culture Medium: Minimum essential medium (MEM) with non-essential amino acids, sodium pyruvate, and 10% fetal bovine serum. The medium was changed twice weekly. A confluent monolayer was achieved in 1 week. The growth medium is prepared as listed below.

| Solution | Volume (ml) |
| --- | --- |
| 1. MEM (Gibco #320-1090AK) With Earle's salts and L-glutamine | 1000 |
| 2. Penicillin (10,000 units/ml), streptomycin (10,000 mg/ml), Gibco #600-5140 PG | 10 |
| 3. MEM sodium pyruvate, 10 mM (100X) Gibco #320-1140 | 10 |
| 4. MEM nonessential amino acids, 10 mM (100X) Gibco #320-1140AG | 10 |
| 5. L-glutamine, 200 mM (100X), Gibco #320-5030AG | 10 |
| 6. Hyclone fetal bovine serum, defined, Hyclone #A-111-L | 100 |

Subculture Procedure: Remove medium, wash with PBS, add fresh trypsin (0.25%)-EDTA (0.02%) with Hank's Balanced Salt solution and let flask stand for a minute and remove the trypsin solution. Incubate flask at 37° C. until cells detached. Add fresh medium, disperse and dispense cells into new flasks. Subcultivation ratio: 1:6.

PREPARATION of Delipidated Serum: Fetal calf serum (100 ml) and CAB-O-Sil (2 grams) stir overnight at 4° C. and centrifuge at 16,000 rpm for 5 hrs. Filter supernatant and store at 4° C.

48 hrs. prior to harvest, switch cells grown in MEM with 10% Fetal Calf serum to MEM with 10% delipidated serum.

3. Harvest: Remove medium, wash with PBS, add fresh trypsin (0.25%)-EDTA (0.02%) with Hank's Balanced Salt solution, rinse and remove. Incubate flask at 37° C. until cells detach. Add 6 ml of MEM medium per flask to suspend cells and combine into centrifuge tube. Spin cells at 1,000 rpm for 5 mins. Wash by resuspending cell pellet in PBS and repeat centrifuging. Count cells ($2.5 \times 10^9$ yield from 18 flasks (75 cm$^2$). Resuspend in 10 mls of 50 mM HEPES (N-[2-Hydroxyethyl]piperazine-N'-[2-ethane-sulfonic acid]) containing 5 mM MgCl$_2$, 2 mM MnCl$_2$, 10 mM DTT, pH 7.5 (enzyme suspension buffer).

4. Cell Extracts: Sonicate (probe sonicator setting #60, pulse) the cell suspension on ice for 2 min. After a 1 min. cooling on ice, the sonication is repeated until greater than 90% of the cells are broken as observed microscopically. Centrifuge cell suspension for 10 mins. at 10,000 rpm. Transfer supernatant to clean tube and centrifuge at 20,000 rpm for 20 mins. The HepG2 enzyme preparation was centrifuged at 34,000 rpm to separate the cytosol and microsomal enzymes. The enzyme suspension was diluted 1 to 250 and used to perform the squalene synthetase assay using 3 μM $^3$H-farnesyl pyrophosphate as the substrate.

Squalene Synthase Assay

Reactions were performed in 1.2 ml polypropylene tube strips of 8. Buffer mixture and subtrate mixture for the assay were prepared from the following solution:

Buffer mixture contains 270 mM HEPES, pH 7.5, 20 mM Potassium fluoride and 5.4 mM Dithiothreitol(DTT). 55 μl of this mixture was used per assay. The final concentrations of HEPES, KF and DTT in the assay are 150 mM, 11 mM and 3 mM respectively.

Substrate mixture

| Stock concentration | μl used per assay | Final concentration |
|---|---|---|
| 1. MgCl$_2$, 20 mM | 10 | 6 mM |
| 2. NADPH, 3 mM (made fresh) | 10 | 1 mM |
| 3. Squalene Epoxidase inhibitor, Banyu FW-439H, 0.5 mg per ml | 0.02 | 1 μg per ml |
| 4. $^3$H-farnesyl-pyrophosphate, 25 mM, 20 Ci per mole | 2.4 | 0.6 μM |
| 5. Farnesyl-pyrophosphate, 3 mM | 0.08 | 2.4 μM |
| 6. Water | 7.5 | |

For each reaction, 55 μl of buffer mixture was taken with 5 μl of an inhibitor solution in DMSO and 10 μl of diluted enzyme (1 to 250 as described in the enzyme preparation, the final protein concentration of enzyme in the assay is 2 μg per ml.). The inhibitor solution was prepared by dissolving dry sample in DMSO. The reaction was initiated by the addition of 30 μl of substrate solution and the mixture was incubated at 30° C. for 20 minutes. The reactions were stopped by the addition of 100 μl of 95% EtOH, vortexed, and 100 μl of a suspension of 1 gram per ml of Bio-Rad AG 1×8 resin (400 mesh, Chloride form) was then added, vortexed. 300 μl of heptane was added to each tube strip and the strips were capped and vortexed for 10 minutes. 150 μl of heptane layer was then removed into a 96 deep well plate and mixed with 150 μl of scintillation fluid and the radioactivity was determined by liquid scintillation counting. The controls were run with 5 μl of DMSO and blanks were run with the addition of 100 μl of 95% EtOH to denature the enzyme before the addition of the substrate mixture to the assay tube.

Percent inhibition is calculated by the formula:

$$\frac{(\text{Control} - \text{Sample}) \times 100}{\text{Control} - \text{Blank}}$$

IC$_{50}$ values were determined by plotting the log of the concentration of the test compound versus the percentage inhibition. The IC$_{50}$ is the concentration of inhibitor that give 50% inhibition as determined from these plots. The IC$_{50}$ of composition A of this invention was found to be <50 nM.

What is claim is:

1. A composition comprising a compound of formula (I):

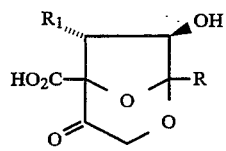

wherein
R is selected from

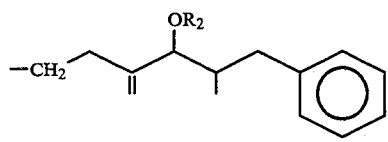

a)

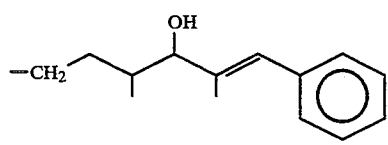

b)

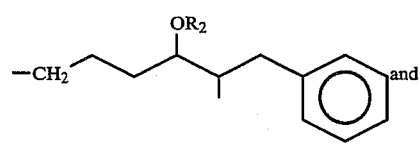

c)

and

R$_1$ is selected from

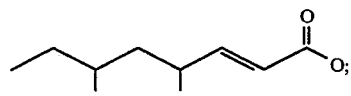

a)

b)

and

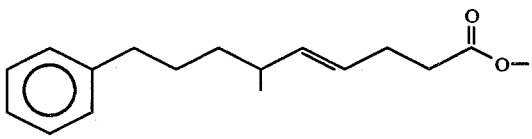

c)

R$_2$ is selected from

H and a)

b)

Provided that when R is

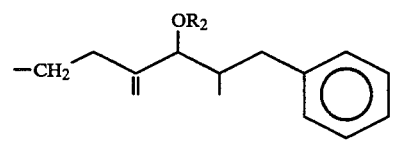

then R$_1$ is

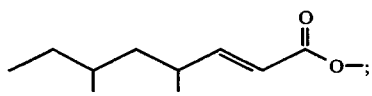

and when R is

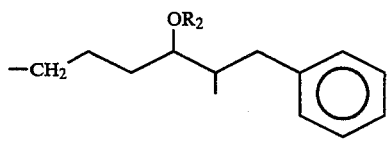

then $R_1$ is

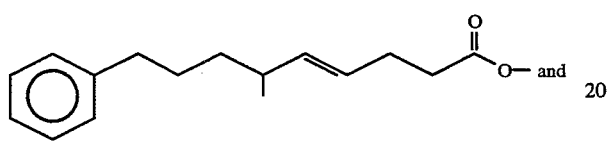

When R is

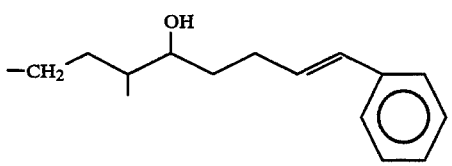

then $R_1$ is

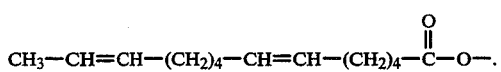

2. The composition of claim 1 wherein R is

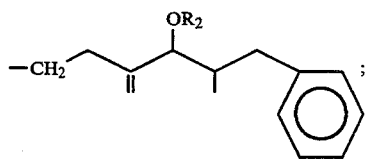

$R_1$ is

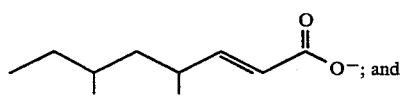

$R_2$ is H or

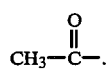

3. The composition of claim 2 wherein $R_2$ is

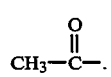

4. The composition of claim 2 wherein $R_2$ is H.

5. A composition comprising a compound of formula (II):

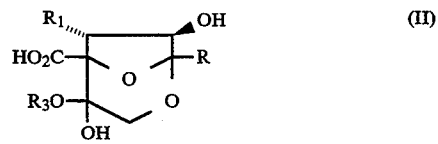

wherein
R is selected from a) 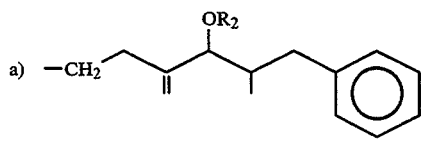

b) 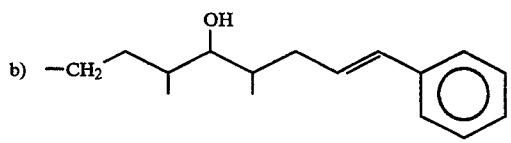

c) 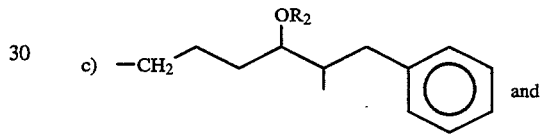
and $R_1$ is selected from a) 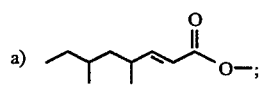

b) 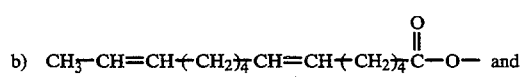 and c) 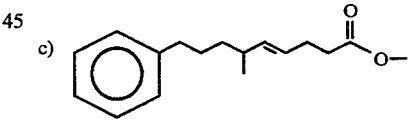

$R_2$ is selected from a) H and b) 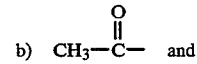 and $R_3$ is $C_{1-5}$alkyl;
Provided that when R is

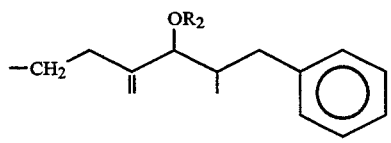

then $R_1$ is

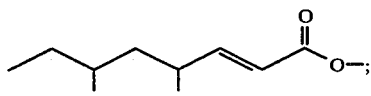

and when R is

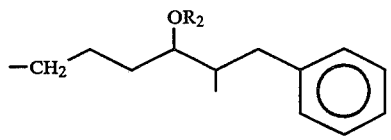

then R₁ is

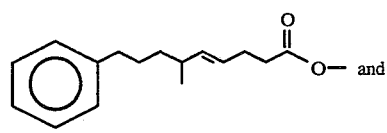

When R is

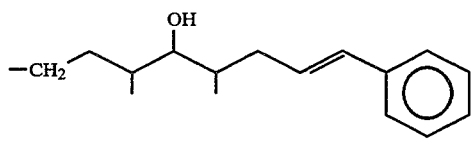

then R₁ is

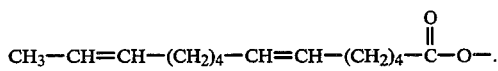

6. The composition of claim 5 wherein R is

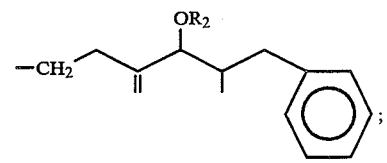

R₁ is

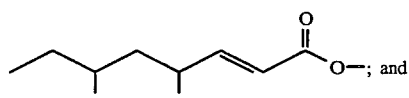

R₂ is H or

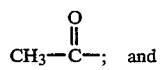

R₃ is CH₃.

7. The composition of claim 6 wherein R₂ is

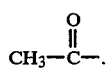

8. The composition of claim wherein R₂ is H.

9. A composition of comprising a compound of formula (III):

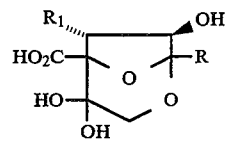

wherein
R is selected from a) 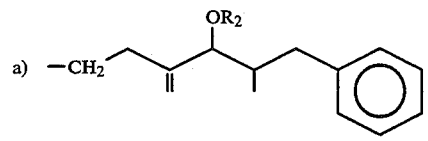

b) (structure with OH)

c) (structure with OR₂)

and

R₁ is selected from a) 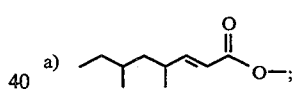

b) 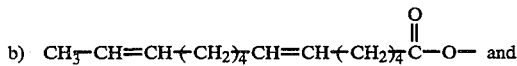

and c) 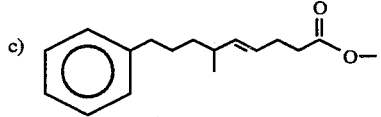

R₂ is selected from a) H and b) 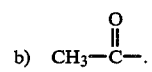

Provided that when R is

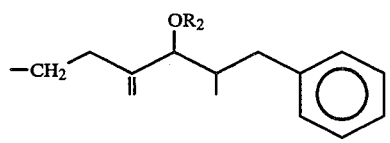

then R₁ is

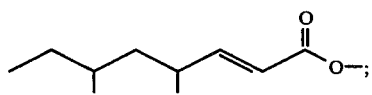

and when R is

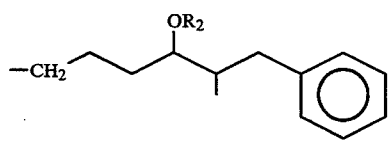

then $R_1$ is

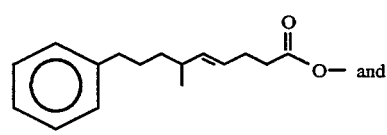

When

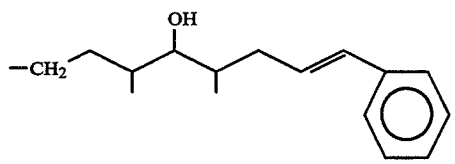

then $R_1$ is

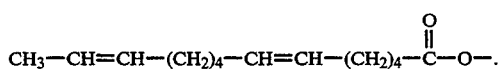

10. The composition of claim 9 wherein R is

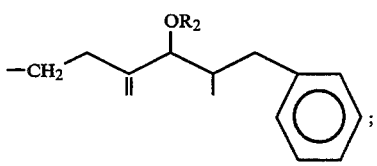

$R_1$ is

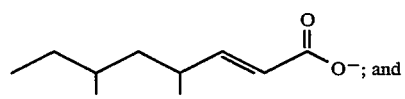

$R_2$ is H or

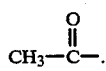

11. The composition of claim 10 wherein $R_2$ is

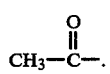

12. The composition of claim 10 wherein $R_2$ is H.

13. A composition comprising a compound of formula (I) and formula (II) and formula (III):

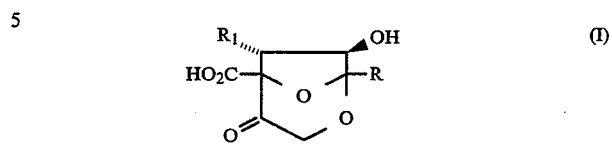 (I)

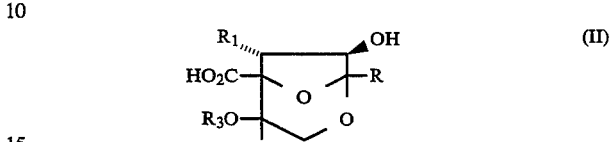 (II)

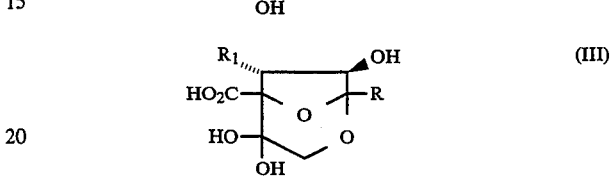 (III)

wherein
R is selected from a) 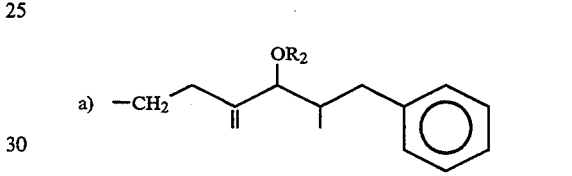

b) 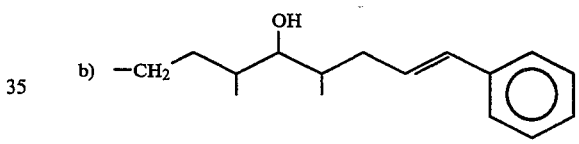

c) 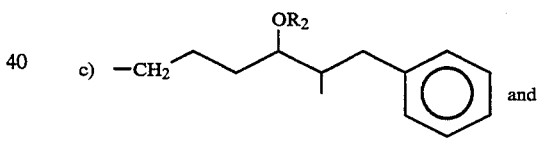 and $R_1$ is selected from a) 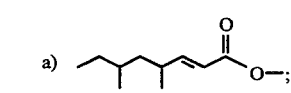

b) 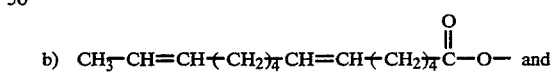 and c) 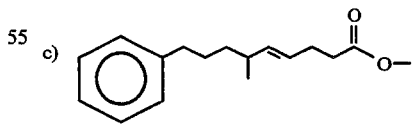

$R_2$ is selected from a) H and b) 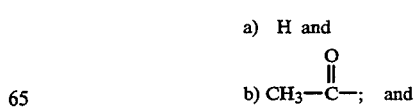 and $R_3$ is $C_{1-5}$alkyl;
Provided that when R is

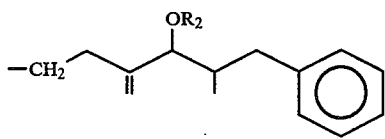
then R₁ is
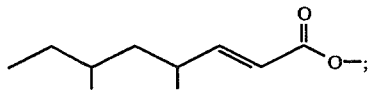
and when R is
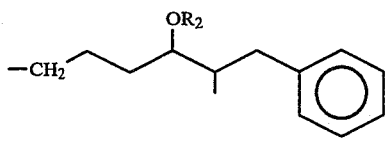
then R₁ is
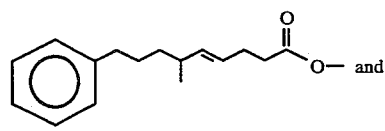
When
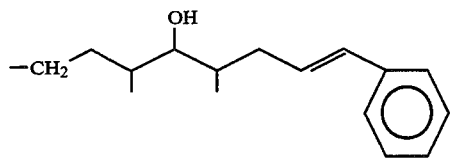
then R₁ is
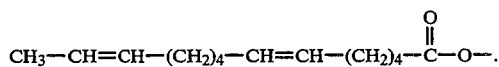
14. A compound of formula (I) substantially free of its equilibrium derivatives of formula (II) and formula (III):
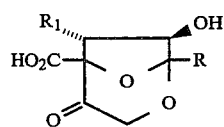 (I)
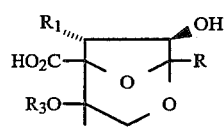 (II)
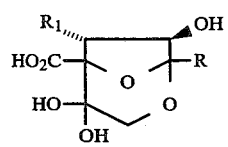 (III)
wherein
R is selected from
a) 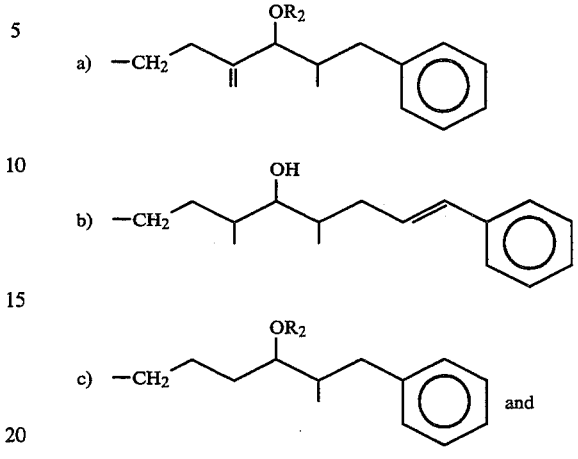
R₁ is selected from
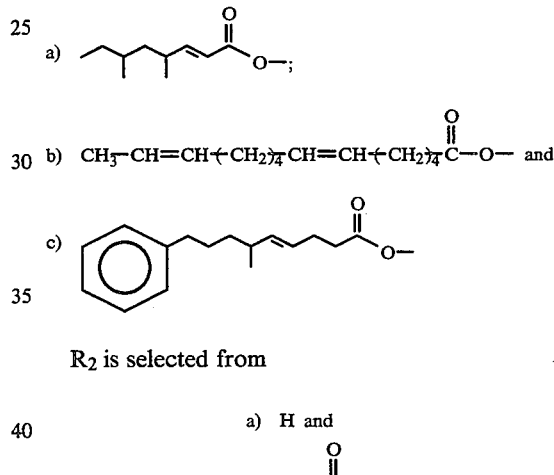
R₂ is selected from
a) H and
b) $CH_3-\overset{O}{\overset{\|}{C}}-$; and
R₃ is $C_{1-5}$alkyl;
Provided that when R is
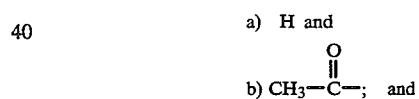
then R₁ is
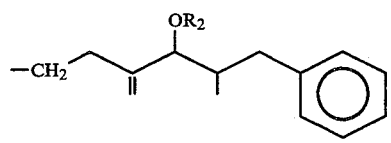
and when R is
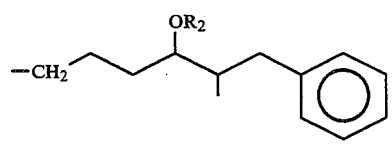

then $R_1$ is
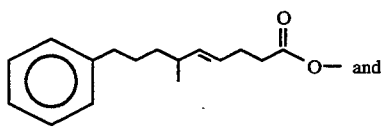
When
R is
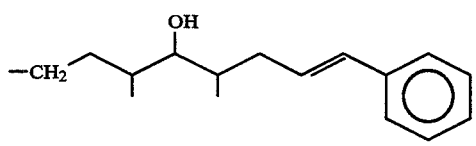
then $R_1$ is
15. A compound of formula (I):
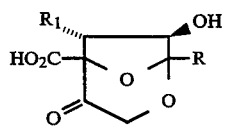   (I)
wherein
R is selected from
a) 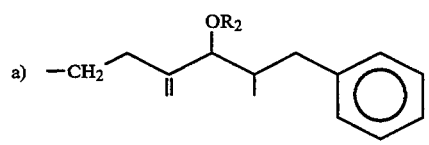
b) 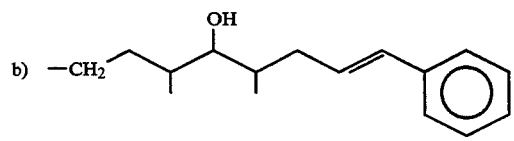
c) 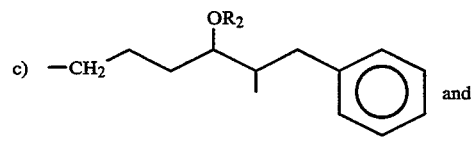 and
$R_1$ is selected from
a) 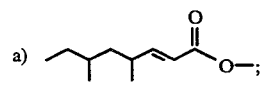
b) 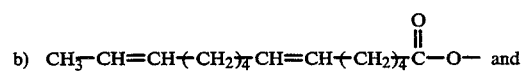 and
c) 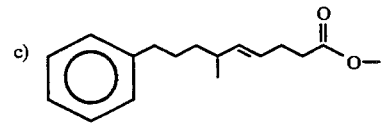
$R_2$ is selected from
a) H and
b) 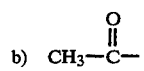
Provided that when R is
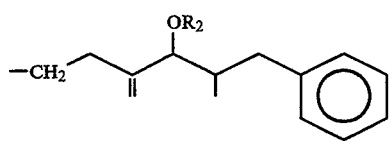
then $R_1$ is
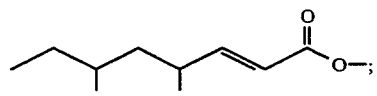
and when R is
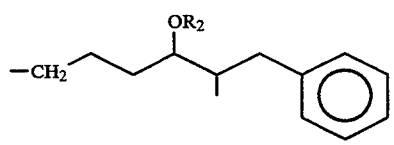
then $R_1$ is
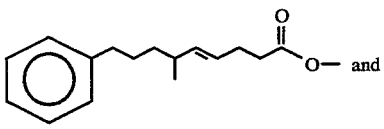
When
R is
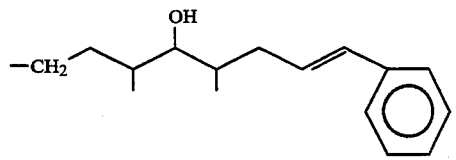
then $R_1$ is
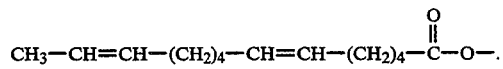
16. The compound of claim 15 wherein
R is
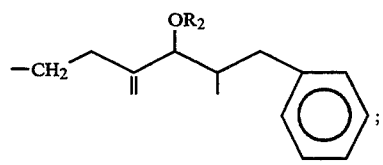;
$R_1$ is R$_2$ is H or $CH_3-\overset{O}{\underset{\|}{C}}-$.

17. The compound of claim 16 wherein R$_2$ is $CH_3-\overset{O}{\underset{\|}{C}}-$.

18. The compound of claim 16 wherein R$_2$ is H.

19. A compound of formula (II):

(II)

wherein
R is selected from a) $-CH_2$- [structure with OR$_2$ and phenyl]

b) $-CH_2$- [structure with OH and phenyl, trans alkene]

c) $-CH_2$- [structure with OR$_2$ and phenyl] and

R$_1$ is selected from a) [branched alkyl with α,β-unsaturated carboxylate] $-O^-$;

b) $CH_3-CH=CH-(CH_2)_4-CH=CH-(CH_2)_4-\overset{O}{\underset{\|}{C}}-O-$ and c) [phenyl-alkyl-methyl-alkene-carboxylate] $-O^-$ R$_2$ is selected from a) H and b) $CH_3-\overset{O}{\underset{\|}{C}}-$; and R$_3$ is C$_{1-5}$alkyl Provided that when R is $-CH_2$- [structure with OR$_2$, =CH$_2$, methyl, and phenyl]

then R$_1$ is

[branched alkyl with α,β-unsaturated carboxylate] $-O-$;

and when R is $-CH_2$- [structure with OR$_2$ and phenyl]

then R$_1$ is

[phenyl-(CH$_2$)$_2$-CH=CH-CH$_2$-carboxylate] $-O-$ and

When R is $-CH_2$- [structure with OH, methyl groups, trans alkene, phenyl]

then R$_1$ is $CH_3-CH=CH-(CH_2)_4-CH=CH-(CH_2)_4-\overset{O}{\underset{\|}{C}}-O-$.

20. The compound of claim 19 wherein R is $-CH_2$- [structure with OR$_2$, =CH$_2$, methyl, and phenyl];

R$_1$ is

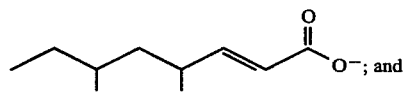
R₂ is H or
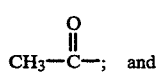
R₃ is CH₃.
21. The compound of claim 20 wherein R₂ is
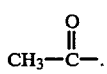
22. The compound of claim 20 wherein R₂ is H.
23. A compound of formula (III):
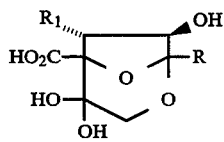
(III)
wherein
R is selected from
a) 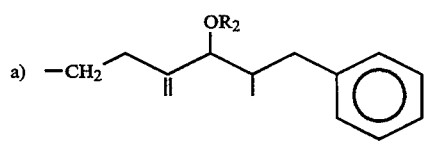
b) 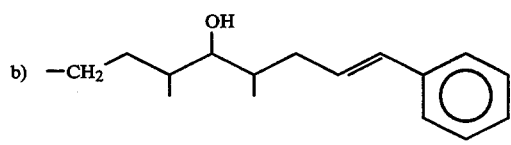
c) 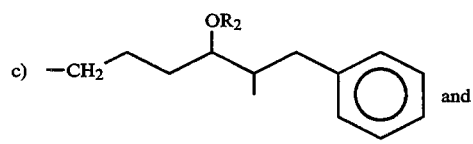 and
R₁ is selected from
a) 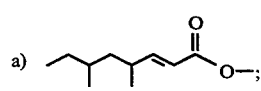
b) 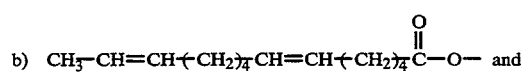 and
c) 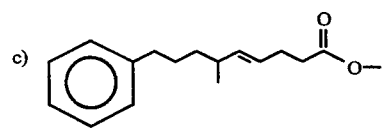
R₂ is selected from
a) H and
b) 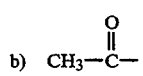
Provided that when R is
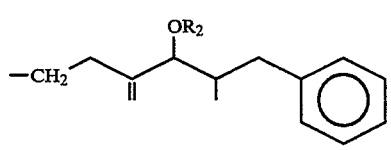
then R₁ is
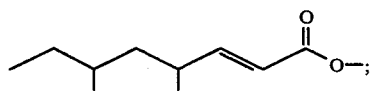
and when R is
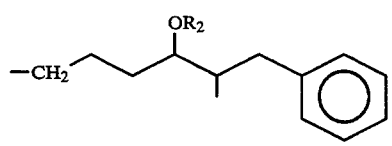
then R₁ is
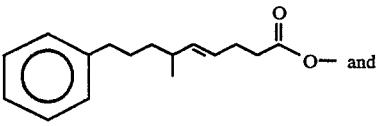 and
When
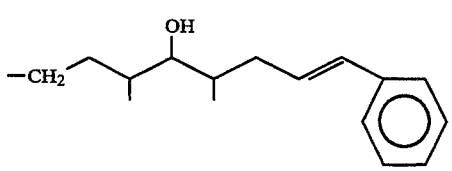
then R₁ is
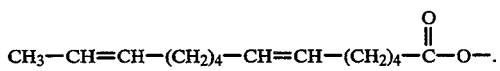
24. The compound of claim 23 wherein R is
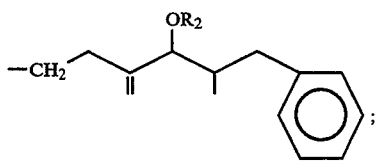
R₁ is

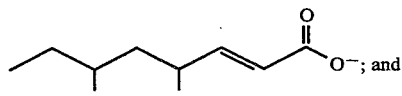
R$_2$ is H or
25. The compound of claim 24 wherein R$_2$ is
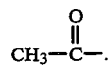
26. The compound of claim 24 wherein R$_2$ is H.
* * * * *